(12) United States Patent
Fargahi et al.

(10) Patent No.: US 8,778,006 B2
(45) Date of Patent: Jul. 15, 2014

(54) DELIVERY SYSTEM HAVING A RELEASE MECHANISM FOR RELEASING AN OBJECT CARRIED BY A CATHETER AS WELL AS A RELEASE MECHANISM OF A DELIVERY SYSTEM

(75) Inventors: Amir Fargahi, Buelach (CH); Raimund Moehl, Forch (CH); Vesna Colic, Buelach (CH); Patrice Bachmann, Winterthur (CH)

(73) Assignee: BIOTRONIK VI Patent AG, Barr (CH)

( * ) Notice: Subject to any disclaimer, the term of this patent is extended or adjusted under 35 U.S.C. 154(b) by 672 days.

(21) Appl. No.: 12/430,191

(22) Filed: Apr. 27, 2009

(65) Prior Publication Data

US 2009/0270969 A1  Oct. 29, 2009

(30) Foreign Application Priority Data

Apr. 26, 2008 (DE) .................. 10 2008 021 060

(51) Int. Cl.
*A61F 2/06* (2013.01)
*A61F 2/95* (2013.01)
*A61F 2/962* (2013.01)
*A61F 2/97* (2013.01)

(52) U.S. Cl.
CPC .......... *A61F 2/95* (2013.01); *A61F 2002/9517* (2013.01); *A61F 2/962* (2013.01); *A61F 2/97* (2013.01)
USPC ...................................... 623/1.11

(58) Field of Classification Search
CPC ... A61F 2/95; A61F 2002/9517; A61F 2/962; A61F 2/97
USPC ............... 623/1.11, 1.12, 1.23; 242/570, 229, 242/590, 571.3, 571.6, 579, 600, 118
See application file for complete search history.

(56) References Cited

U.S. PATENT DOCUMENTS

| 5,346,498 A | * | 9/1994 | Greelis et al. ................. 606/108 |
| 5,690,644 A | * | 11/1997 | Yurek et al. ................... 623/1.11 |
| 6,533,811 B1 | | 3/2003 | Ryan et al. |
| 6,599,296 B1 | * | 7/2003 | Gillick et al. ................. 606/108 |
| 6,673,101 B1 | * | 1/2004 | Fitzgerald et al. ........... 623/1.11 |

(Continued)

FOREIGN PATENT DOCUMENTS

| DE | 19936207 A1 | 2/2001 |
| DE | 60011355 T2 | 7/2005 |
| DE | 102006004123 A1 | 8/2007 |
| EP | 0747021 A2 | 12/1996 |
| EP | 1447058 A1 | 8/2004 |
| EP | 1844739 A1 | 10/2007 |
| WO | 2009091603 A1 | 7/2009 |

OTHER PUBLICATIONS

Search Report for European Patent Application No. 09156301.5; Aug. 17, 2009.
Search Report for German Patent Application No. 10 2008 021 060.9; Mar. 11, 2009.

*Primary Examiner* — Darwin Erezo
*Assistant Examiner* — Katrina Stransky
(74) *Attorney, Agent, or Firm* — Greer, Burns & Crain, Ltd.

(57) ABSTRACT

A delivery system having a release mechanism (70) for releasing an object (12), in particular, a supporting body, which is carried by the catheter (20), whereby the catheter (20) has at least one outer shaft (50) which is relatively displaceable toward the object (12) to release the object (12). The catheter (20) has a winding device (100) on its proximal end (24) which winds up a proximal section (52) of the outer shaft (50) to create a relative displacement of the outer shaft (50).

20 Claims, 7 Drawing Sheets

(56) References Cited

U.S. PATENT DOCUMENTS

| | | |
|---|---|---|
| 6,866,669 B2 | 3/2005 | Buzzard et al. |
| 2004/0098083 A1* | 5/2004 | Tran et al. .................... 623/1.11 |
| 2005/0080476 A1* | 4/2005 | Gunderson et al. .......... 623/1.11 |
| 2005/0256562 A1* | 11/2005 | Clerc et al. ................... 623/1.11 |
| 2006/0283998 A1* | 12/2006 | Ono ............................... 242/250 |
| 2007/0219617 A1* | 9/2007 | Saint ............................ 623/1.12 |
| 2007/0244540 A1* | 10/2007 | Pryor ........................... 623/1.11 |
| 2008/0091137 A1* | 4/2008 | Reavill ............................ 604/27 |
| 2010/0036472 A1* | 2/2010 | Papp ............................ 623/1.11 |

* cited by examiner

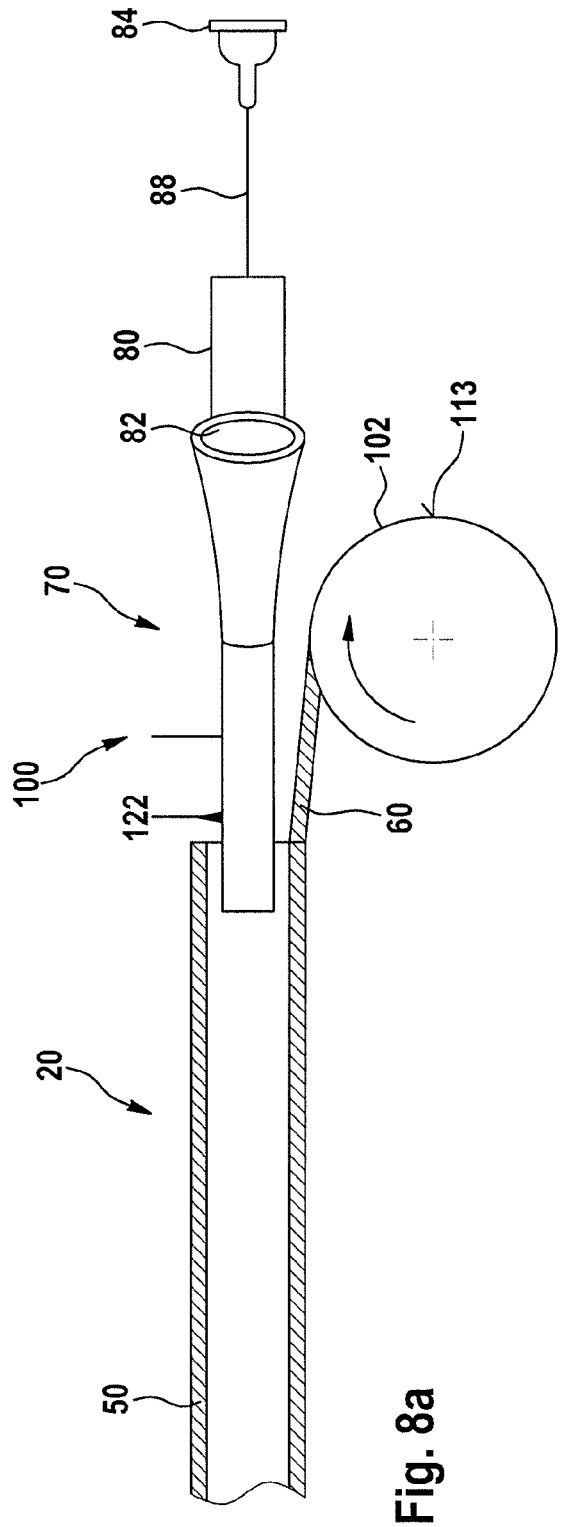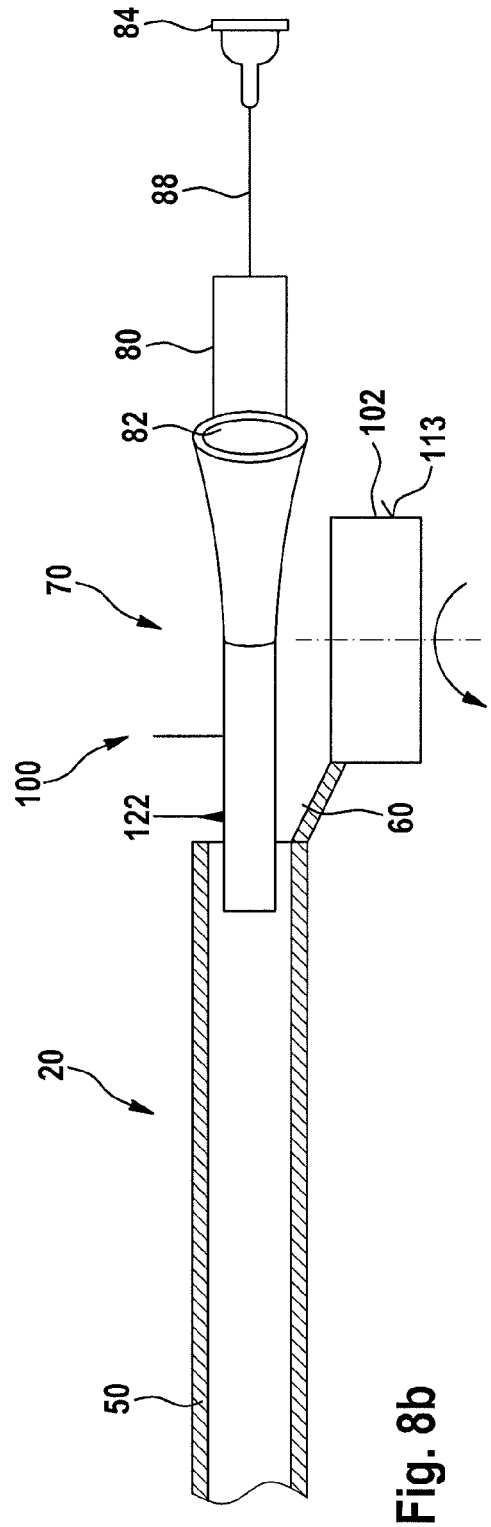

DELIVERY SYSTEM HAVING A RELEASE MECHANISM FOR RELEASING AN OBJECT CARRIED BY A CATHETER AS WELL AS A RELEASE MECHANISM OF A DELIVERY SYSTEM

PRIORITY CLAIM

This patent application claims priority to German Patent Application No. 10 2008 021 060.9, filed Apr. 26, 2008, the disclosure of which is incorporated herein by reference in its entirety.

FIELD

The present disclosure relates to a delivery system having a release mechanism for releasing an object carried by a catheter. The present disclosure also relates to a release mechanism of a delivery system.

BACKGROUND

It is known that catheters may be used for releasing objects, e.g., stents, or for use of dilatation balloons. One field of application is in angioplasty, for example, where balloon catheters are inserted into blood vessels and advanced up to a stenosis, where the balloon catheters are dilated to eliminate the stenosis of the blood vessel. A small-diameter guide wire usually protrudes beyond the balloon catheter at the distal end.

German Patent Application No. 600 11 355 discloses a delivery system for an intravascular prosthesis with which the proximal end of a catheter engages in a running device which facilitates a relative displacement between an inner sheath and an outer sheath of the catheter. For releasing an object such as a stent arranged on the distal end, the outer sheath is pulled toward the proximal end. This movement may take place uniformly by pulling the outer sheath into the running device.

Such delivery systems are also known from European Patent Application No. 1 447 058; U.S. Pat. No. 6,866,669; and European Patent Application No. 747 021 which are cited herein as examples.

With the approaches known previously, there is a dependence between the total length of the catheter and the length of the stent. The longer the stent, the longer the total length of the catheter. For example, this yields a total length of a catheter with a stent length of 200 mm, which is at least 180 mm longer than the length of a catheter with a stent length of 20 mm. Accordingly, for the user, e.g., the physician, inserting the catheter this means using a longer guide wire with more complex and less ergonomic handling.

SUMMARY

The present disclosure describes several exemplary embodiments of the present invention.

One aspect of the present disclosure provides a delivery system having a release mechanism for releasing an object which is carried by a catheter, whereby the catheter has at least one outer shaft displaceable relatively toward the object to release said object, wherein the catheter, on its proximal end (24), has a winding device which winds up a proximal section of the outer shaft to create a relative displacement of the outer shaft.

Another aspect of the present disclosure provides a release mechanism of a delivery system (10) for releasing an object (12), in particular a supporting body, according to claim 1, said the object being carried by a catheter (20) on its distal end (22), whereby the catheter has at least one outer shaft (50) which is relatively displaceable toward the object (12) for releasing same the object, characterized by the release mechanism comprising a winding device (100), which winds up a proximal section (52) of the outer shaft (50) to create a relative displacement of the outer shaft (50)

A further aspect of the present disclosure provides a delivery system for releasing an object carried by a catheter, the delivery system comprising a) a catheter having a proximal end, a distal end and at least one displaceable outer shaft having a proximal section; b) a release mechanism for releasing an object carried by the catheter; and, c) a winding device associated with the proximal end of the outer shaft, the winding device being capable of winding up the proximal section of the outer shaft so as to create a relative displacement of the outer shaft.

The present disclosure provides a delivery system having a release mechanism for an object to be released as well as a release device of a delivery system which permits easy and ergonomic handling.

The present disclosure provides a delivery system having a release mechanism for releasing an object, in particular, a stent body, which is carried by a catheter, such that the catheter has at least one outer shaft which is displaceable relatively toward the object to release it.

It is proposed that the catheter shall have a winding device on its proximal end to wind up a proximal section of the outer shaft to create a relative displacement of the outer shaft. The winding induces a sliding movement in the outer shaft which moves the outer shaft away from the distal end of the catheter to the proximal end. The sliding movement may take place in a controlled and precise manner. The winding allows a compact design of the catheter with a length that is independent of the length of the object to be released, e.g., a stent. Likewise, the winding device can relieve the burden on the user and can at least partially assume the propulsion force for retraction of the outer shaft in releasing the object. The release may take place in a very controlled and accurate manner. When the winding device is motorized, the displacement of the outer shaft may proceed continuously and uniformly. It is likewise conceivable that a variable displacement rate can be implemented manually or with automation to retract the outer shaft more slowly at the start of its release and retract it more rapidly toward the end of its release.

The release mechanism preferably has a cutting device which can cut the section of the outer shaft that is moved toward the proximal end of the catheter. The cutting device may preferably have at least one cutting blade which cuts the outer shaft in the axial direction. By cutting the outer shaft, the free end of the outer shaft may be gripped in the winding mechanism and wound up. This makes it possible to avoid having to design the catheter to be longer, e.g., in supporting bodies such as stents having a longitudinal extent greater than is the case with shorter supporting bodies to guarantee a more reliable release of the stent body. The catheter may be designed independently of the length of the supporting body. In the manufacture of catheters for different objects, such as stents, to be released, inexpensive identical parts may be used.

The release mechanism may advantageously form a handle part of the catheter. This allows especially ergonomic handling of the catheter. Likewise, the release mechanism may form a T-shaped body as an end piece of the catheter.

The winding mechanism may preferably comprise a roller arranged at one end of the catheter. A cut may be formed in the outer shaft, and the cut shaft lateral surface may be wound up by the winding mechanism.

As an alternative, the winding mechanism may comprise at least two rollers arranged, preferably symmetrically, on the catheter. At least two cuts can be produced here and the cut section of the outer shaft may be divided into separate surface areas, each being gripped and wound up separately by the winding mechanism. This facilitates the winding, which can be performed with little expenditure of force.

In addition, the present disclosure relates to a release mechanism for a delivery system for releasing an object, in particular, a stent body, which is carried by a catheter on its distal end, whereby the catheter has at least one outer shaft which is displaceable relative to the object to thereby release the object.

A winding device is provided which winds a proximal section of the outer shaft to produce a relative displacement of the outer shaft. The winding induces a sliding movement in the outer shaft away from the distal end of the catheter toward the proximal end. The sliding movement may take place in a controlled and precise manner. The object may be released in a very controlled and accurate manner because the small dimension of the handling part advantageously allows optimum handling. In the case when the winding device is motorized, the displacement of the outer shaft may take place continuously and uniformly. It is likewise conceivable for a variable displacement rate to be manually implementable or automated so as to retract the outer shaft more slowly at the start of its release for more accurate positioning of the outer shaft and more rapidly toward the end of its release. The winding device may advantageously be connected to a conventional catheter.

A cutting device may preferably be connected to the winding device so that the section of the outer shaft moved toward the proximal end of the catheter can be cut when the outer shaft is moved toward the proximal end to release the object on the distal end of the catheter.

At least one roller may be provided in the winding device so that the outer shaft can be wound onto the roller in at least some areas.

If the at least one roller may have a smaller diameter on one axial end than on the opposite axial end, then the outer shaft may be moved at a variable rate with a constant rotational speed.

Improved handling is obtained when the at least one roller can be locked by a locking mechanism. This allows a defined start of the release and good control of the movement of the outer shaft, which can also be interrupted in a controlled manner.

The winding device for rolling up the shaft may advantageously be connected to a spring element so that the winding and/or the movement of the outer shaft can be supported by the spring force. This allows especially simple and controlled handling of the winding device.

The winding device for winding up the outer shaft may be drivable by hand, e.g., with a crank element.

The winding device may alternatively or additionally comprise an electric drive for winding up the outer shaft. The winding of the outer shaft may take place in this way without application of force by the user.

The winding device may have an operating element which, in a first position, releases the at least one roller for execution of a rotational movement and, in another position, blocks the at least one roller. A defined and controlled movement of the outer shaft may advantageously be achieved in this way.

BRIEF DESCRIPTION OF THE DRAWINGS

Various aspects of the present disclosure are described hereinbelow with reference to the accompanying figures.

FIG. 8a shows a third exemplary embodiment of a preferred delivery system with rollers oriented in relation to a catheter;

FIG. 8b shows a fourth exemplary embodiment of a delivery system with rollers oriented in relation to a catheter;

FIG. 10b shows a detail of the release mechanism shown in FIG. 10a.

DETAILED DESCRIPTION

Figure 1:
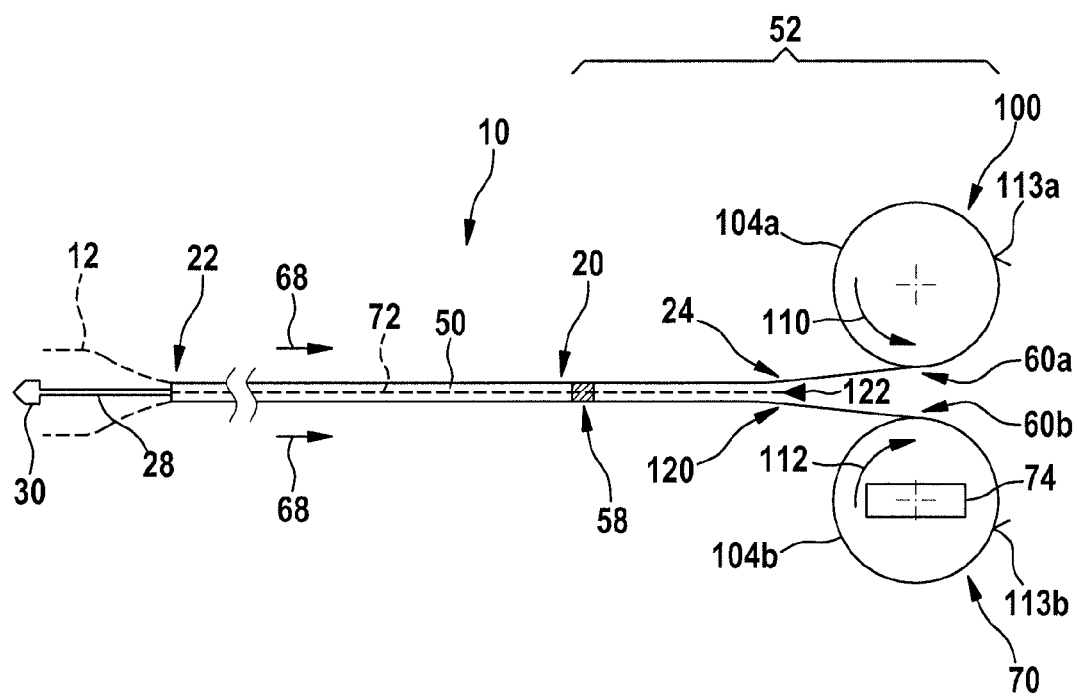
FIG. 1 shows a first exemplary embodiment having a winding device for winding up a cut outer shaft to release a stent at a distal end of a catheter.

Elements in the figures that are functionally the same or have the same effect are labeled with the same reference numerals. The figures show schematic diagrams of the present invention. The figures represent nonspecific parameters of the present invention. In addition, the figures illustrate only typical exemplary embodiments of the present disclosure and should not limit the disclosure to the exemplary embodiments depicted here.

To avoid unnecessary repetition, when elements in a figure are not described in detail, reference is made to the respective description of the elements in the preceding figures.

FIG. 1 shows a first exemplary embodiment of the present disclosure having a first delivery system 10 with a release mechanism 70 for releasing an object 12, in particular, a supporting body carried on a distal end 22 of a catheter 20, such that the catheter 20 has at least one outer shaft 50 which is relatively displaceable toward the object 12 to release the object 12 in a pulling direction 68.

The catheter 20 has a winding device 100 on its proximal end 24 which winds a proximal section 52 of the outer shaft 50 to create the relative displacement of the outer shaft 50. The proximal section 52 of the outer shaft 50 corresponds to the length of the object 12, which may be a self-expanding stent, for example. For purposes of the present disclosure, the terms "proximal" and "distal" refer to the position of the user, so the proximal end 24 is near the user, while the distal end 22 is remote from the user.

The outer shaft 50 is arranged around an inner shaft 28, with a tip 30 being provided on the distal end 22 of the catheter 20 for guiding the catheter 20 over a guide wire in the usual manner, such that the object 12 surrounds the inner shaft 28 and is adapted for insertion into a blood vessel, for example, within the outer shaft 50.

In this exemplary embodiment, the winding device 100 comprises two rollers 104a, 104b which are arranged symmetrically with the catheter 20 and/or the outer shaft 50 and can be driven by a drive (not shown here), e.g., a crank or an electric motor.

The releasing mechanism 70 comprises, in addition to the winding device 100, a cutting device 120 having at least one cutting blade 122 with which the section 52 of the outer shaft 50 that is moved toward the proximal end 24 of the catheter 20 can be cut along the longitudinal extent 72 of the outer shaft 50. When using two rollers 104a, 104b, a symmetrical separation of the outer shaft 50 into two parts 60a, 60b is expedient.

The outer shaft 50 may be cut on the proximal end of the catheter 20 and its ends attached to the rollers 104a, 104b. When the rollers 104a, 104b are rotated, the parts 60a, 60b are placed on a lateral surface 113a (roller 104a) and/or 113b (roller 104b) of the rollers 104a, 104b and secured at the ends 66a, 66b, which is shown more clearly in the detail in FIG. 2.

At the same time, this leads to a displacement of the outer shaft 50 in the direction of the rollers 104a, 104b such that the cutting device 120 continues to cut the section 52 until reaching a stop element 58, for example. Cutting may also be stopped by allowing only a limited number of revolutions of rollers 104a, 104b.

Rollers 104a, 104b are rotated in the opposite direction of rotation 110, 112. For example, roller 104a rotates counterclockwise and roller 104b rotates clockwise. The rotation may be accomplished with a drive 74, e.g., by a hand-operated crank or an electrically operated drive (not shown).

Figure 4A:
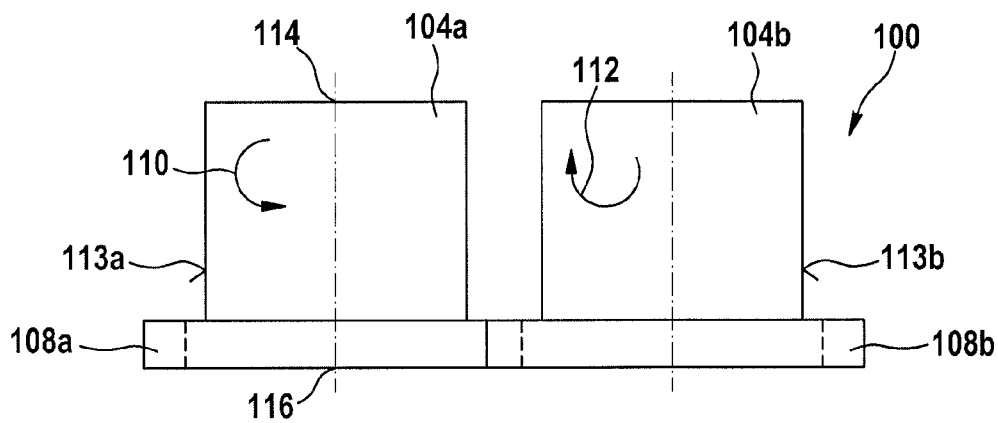
FIG. 4a shows a detailed side view of two cooperating rollers of a preferred winding device.
Figure 4B:
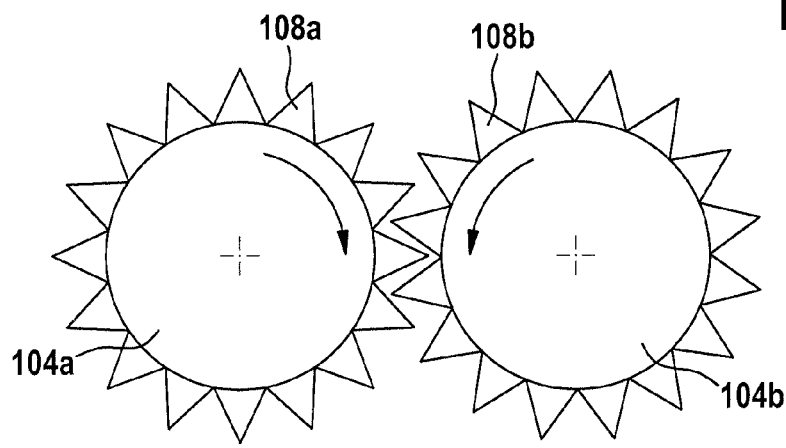
FIG. 4b shows a detailed top view of two cooperating rollers of a preferred winding device.

When the drive 74 on the roller 104b is activated and rotation of the roller is induced, another roller 104a may also be moved due to a favorable design of the winding device 100 (FIGS. 4a and 4b). To do so, gearwheel 108a, 108b is arranged on one end of each roller 104a, 104b. The gearwheels 108a, 108b intermesh so that the movement of one roller, e.g., 104b, induces movement of the other roller, e.g., 104a, and symmetrical winding is possible (FIGS. 4a and 4b).

Figure 3:
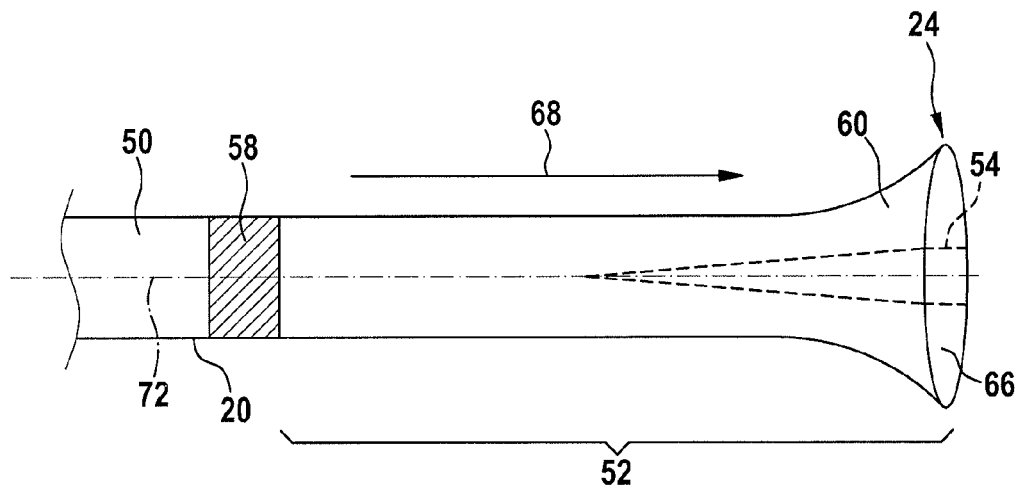
FIG. 3 shows a second exemplary embodiment having an outer shaft cut at one end.

FIG. 3 shows another exemplary embodiment of the present disclosure in which, instead of making several cuts in the outer shaft 50, only a one-sided cut 54 is made from a proximal free end 66 of the outer shaft 50 up to a stop element 58 along the longitudinal extent 72 of the catheter 20. The winding device (not shown here) then preferably has only a single roller for winding up the outer shaft 50, as explained in greater detail in the exemplary embodiment in FIGS. 7a and 7b.

Figure 5:
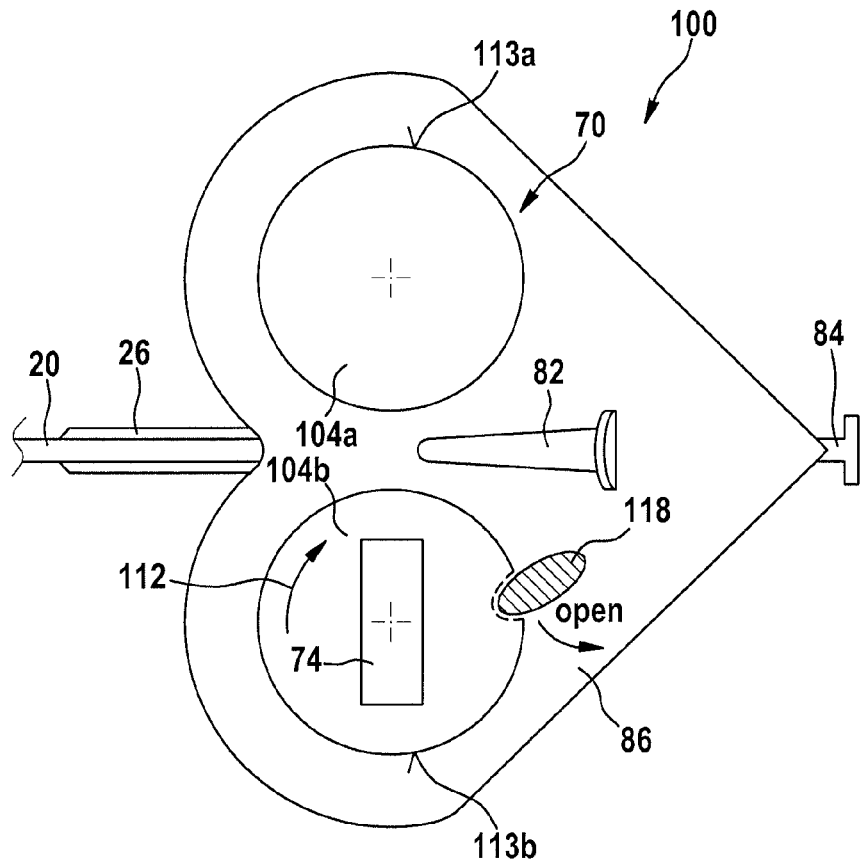
FIG. 5 shows a top view of a delivery system with a preferred winding device.
Figure 6:
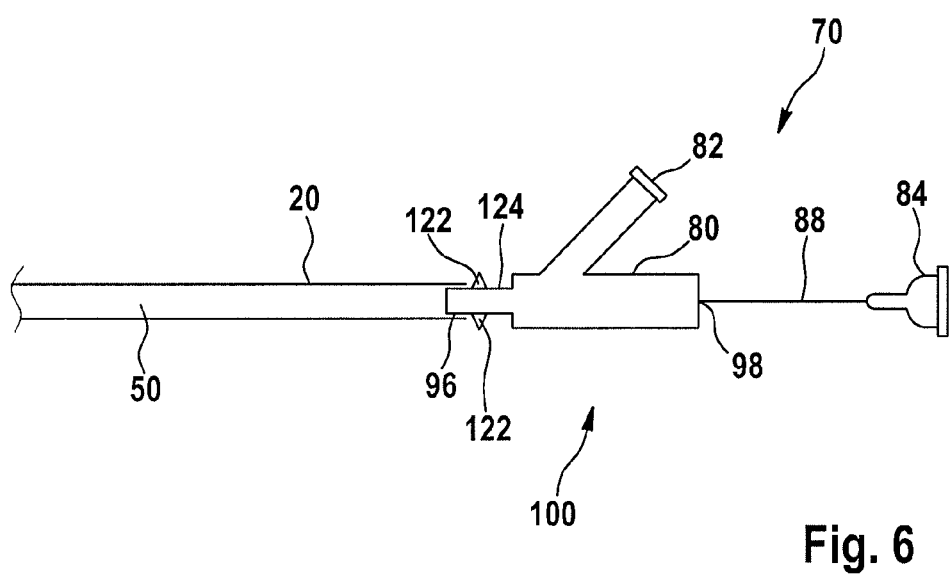
FIG. 6 shows a side view of the delivery system shown in FIG. 5 without the housing and winding device.

FIG. 5 shows a preferred release mechanism 70 having two rollers 104a, 104b in a housing 86 as seen from above, and FIG. 6 shows an end body 80 of the catheter 20 in a side view with the housing 86 having the release mechanism 70 arranged thereon (the housing and winding device are not shown in the side view in FIG. 6). The end body 80 may also be integrated into the housing 86 of the release mechanism 70.

The rollers 104a, 104b are situated symmetrically with one another and rotate in opposite directions when operated. The rollers 104a, 104b may be secured or released with a locking mechanism 118 on one of the rollers 104b. The inner shaft 28 of the catheter 20 (FIG. 1) may be secured, for example, by means of a metal shaft 88 (FIGS. 6, 8a and 8b) in the housing 86. For stabilization, a kink guard 26 sheathing the catheter 20 is provided on the catheter 20 adjacent to the housing 86.

A connection 82, e.g., in the form of a Luer lock, serves to provide a conventional rinsing of the space between the inner shaft 28 and outer shaft 50. A connection 84 on the free end is optionally also designed as a Luer lock and serves to insert a guide wire and to rinse this area. Distally from the connection 82, two symmetrically positioned cutting blades 122 are arranged on a shoulder 124 of the end body 80 to cut the outer shaft 50 from the inside out in retraction. An arrangement in which the outer shaft 50 is cut longitudinally with exterior cutting blades (not shown) would also be conceivable. Distally and proximally, seals 96 and 98 are arranged at each end of the end body 80 to seal the space between the inner shaft 28 and the outer shaft 50 and/or the metal shaft 88 and the end body 80 and/or outer shaft 50.

Figure 2:
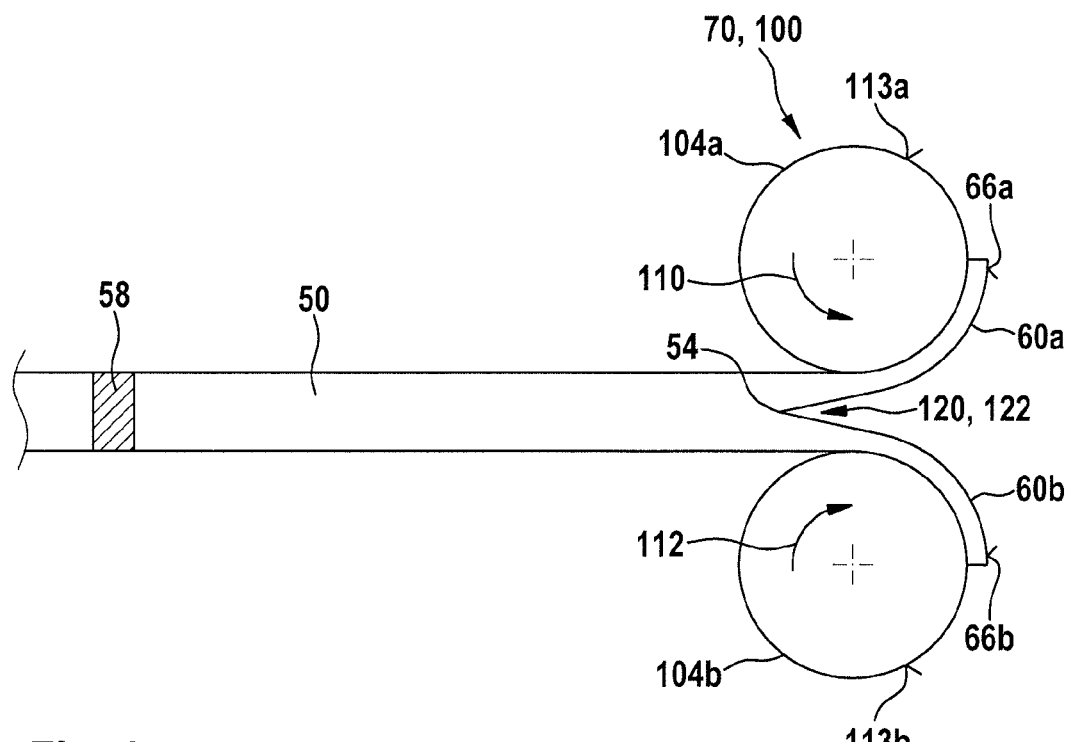
FIG. 2 shows a detail of the exemplary embodiment shown in FIG. 1.

The outer shaft 50, which is already partially slotted, is attached to the rollers 104a, 104b at the lateral surfaces 113a, 113b for winding, as indicated in FIGS. 1 and 2. By rotating the rollers 104a, 104b, the outer shaft 50 is wound up and automatically retracted toward the proximal end 24 of the catheter 20. The object 12 (FIG. 1), e.g., a self-expanding stent, is thereby released.

Figure 7A:
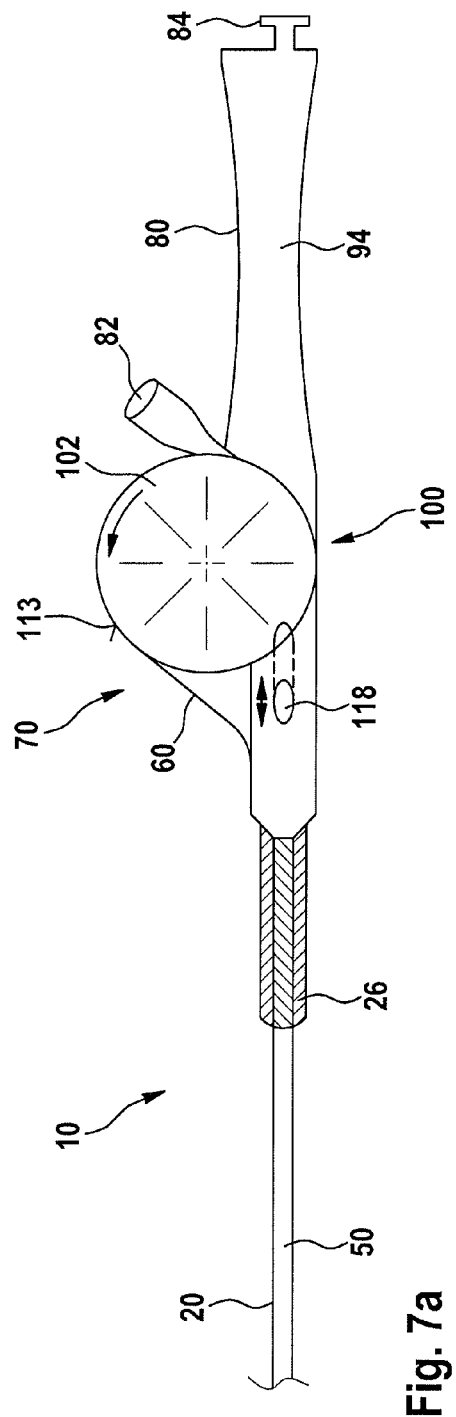
FIG. 7a shows an exemplary embodiment of a delivery system with rollers oriented differently with respect to a catheter.
Figure 7B:
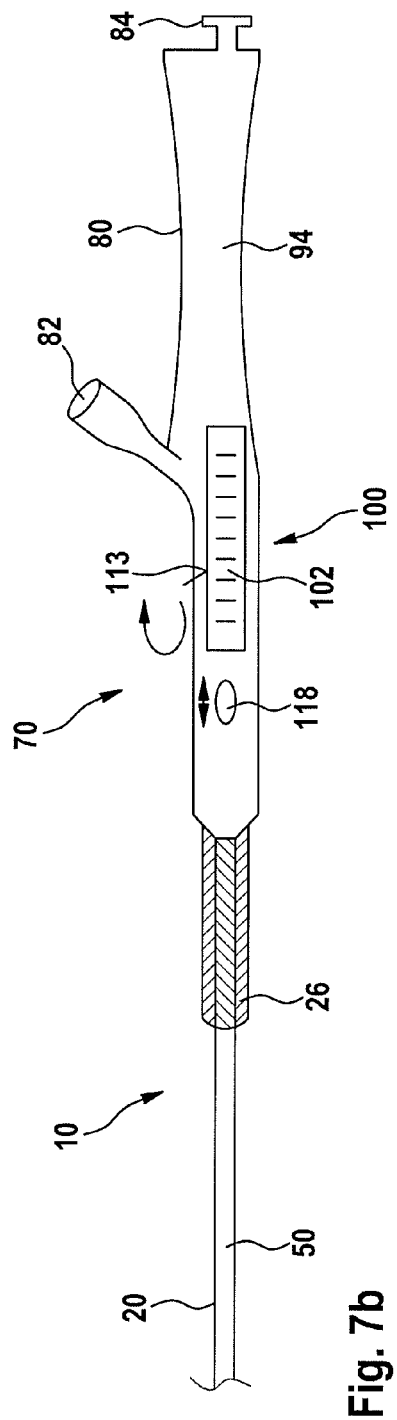
FIG. 7b shows an exemplary embodiment of a preferred delivery system with rollers oriented with respect to a catheter.

FIGS. 7a and 7b illustrate schematically additional preferred exemplary embodiments of a delivery system 10 having a release mechanism 70 comprising a winding device 100 which has only one roller 102 and comprises a one-sided cutting device, as diagrammed schematically in FIG. 3. The roller 102 is arranged on the catheter 20 at one end. The release mechanism 70 is integrated into an end body 80 of the catheter 20 and forms a handle part of the catheter 20, having a handle area 94 which the user can hold in his hand. The roller 102 may be rotated either clockwise or counterclockwise such that rotation in only one direction is allowed for the user and rotation in the opposite direction is blocked.

The catheter 20 is provided with a kink guard 26 on the outside circumference, protrudes into the end body 80 and may be attached with a metal shaft on the end body 80 as described hereinabove.

FIG. 7a shows an exemplary embodiment in which the roller 102 of the winding device 100 is upended so that the roller 102 stands with its circular surface next to and parallel to the catheter 20. FIG. 7b shows a second exemplary embodiment in which the catheter 20 is arranged tangentially to the roller 102. The cutting device is not shown explicitly.

The roller 102 can be secured with a locking mechanism 118 designed as a slide that can move back and forth, for example, and is secured or released as indicated by a double arrow. Roller 102 is arranged distally from the handle area 94 of the end body 80. In both exemplary embodiments, the user holding the end part by the handle area 94 will rotate the roller 102, e.g., with his thumbs, thus allowing one-handed operation of the release mechanism 70 and/or the winding device 100 of the delivery system 10. The cutting can be stopped with a stop element 58 (FIGS. 1, 2 and 3) or by allowing only a limited number of revolutions of the roller 102.

FIGS. 8a and 8b show another exemplary embodiment of the present disclosure with an end body 80 designed as a T-shaped body in which the roller 102 is arranged tangentially to the winding device 100 (FIG. 8a) or parallel and next to the catheter 20 and/or the end body 80 (FIG. 8b).

Figure 9:
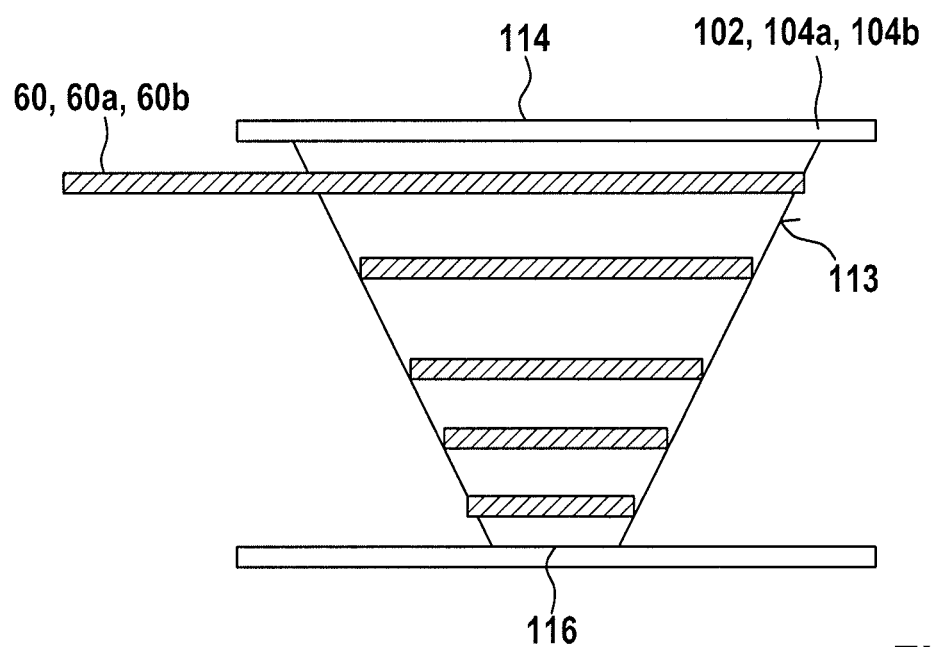
FIG. 9 shows an exemplary embodiment of a roller of a winding device.

In the exemplary embodiments of the winding device 100 described hereinabove, rollers 102, 104a, 104b may have a cylindrical lateral surface 113 or a tapered conical shape, as illustrated in FIG. 9. At one axial end 114, the roller 102, 104a, 104b has a larger diameter of the lateral surface 113 than on its opposing axial end 116. As a result, the parts 60, 60a, 60b of the outer shaft 50 are wound up at different rates at a constant rotational speed of the roller 102, 104a, 104b, depending on the axial height at which the parts 60, 60a, 60b are deposited. At the start of the release, the shaft may be wound onto the thinner end of the roller 102, 104a, 104b, so that the outer shaft 50 is retracted at a lower rate. Toward the end of the release, the shaft is wound onto the thicker end of the roller 102, 104a, 104b, which causes a faster movement of the outer shaft 50.

Figure 10A:
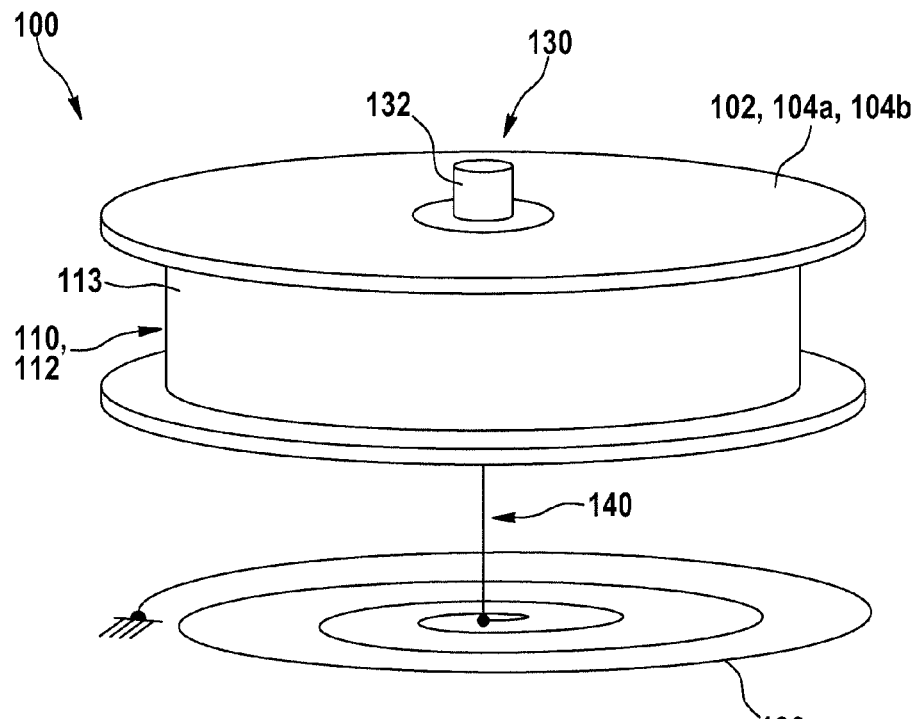
FIG. 10a shows a release mechanism of a winding device with a roller.
Figure 10B:
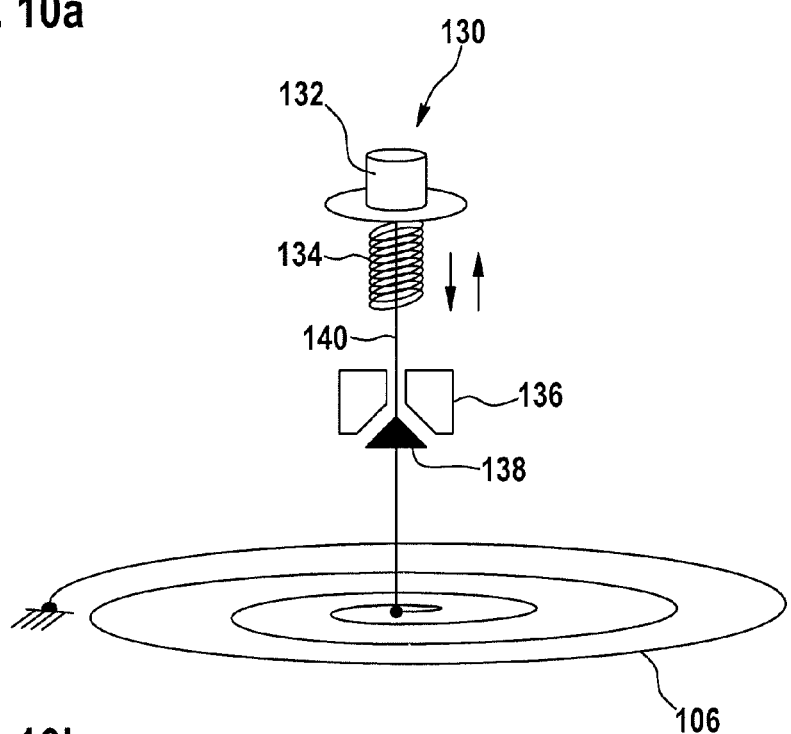

FIGS. 10a and 10b show a detail of a winding device 100 in which the roller 102, 104a, 104b can be rotated mechanically or electrically with a release mechanism 130. The release mechanism extends along a central axis 140 of the roller 102, 104a, 104b. An operating element 132 may be moved outward against the spring force of a spring element 134, which is designed as an axial spring, for example. Through this movement, a mating element 138 is moved out of a brake 136 and the axle 140 is thus released. The brake 136 may comprise brake shoes, for example, with which the mating element 138 engages when the roller 102, 104a, 104b is blocked. The axle 140 is connected to a spring element 106, which is designed as a rotary spring and can induce a rotational movement in the axle 140 and thus in the rollers 102, 104a, 104b when the mating element 138 is uncoupled from the brake 136. An electric drive may also be provided instead of the spring element 106. The reel 102, 104a, 104b may be operated by pushbutton and offers the possibility of achieving different winding speeds. For example, cutting can be stopped by allowing only a limited number of revolutions of the rollers 102, 104a, 104b and/or allowing only a limited movement of the spring element 106.

On the whole, cutting and winding the outer shaft 50 make it possible to provide a short handling part of the catheter 20. This advantageously results in simpler handling and a shorter displacement pathway of the catheter 20 over the guide wire. In addition, the simplification of the release process, in particular, by simple pushbutton operation of the release mechanism, allows more accurate and more homogeneous positioning of the object, e.g., a stent in a blood vessel.

All patents, patent applications and publications referred to herein are incorporated by reference in their entirety.

What is claimed is:

1. A delivery system having a release mechanism for releasing an object which is carried by a catheter having a proximal and a distal end, the object at the distal end of the catheter, the release mechanism comprising: at least one outer shaft retractable toward the proximal end of the catheter to release the object, a stationary cutting device which can cut a proximal section of the outer shaft that is moved toward the proximal end of the catheter into at least two pieces, and a winding device comprising a pair of rollers associated with the proximal end of the catheter which winds up the proximal sections of the outer shaft after the proximal sections are cut to retract the outer shaft toward the proximal end of the catheter, at least one of the rollers having an operating element, a spring connecting the operating element with a brake, wherein when the operating element is in a first position, the brake holds an axel of the at least one roller preventing rotation, and wherein when the operating element is in a second position, the brake releases the axel permitting rotation.

2. The delivery system of claim 1, wherein the cutting device has at least one cutting blade which can cut the outer shaft in the axial direction.

3. The delivery system of claim 1, wherein the release mechanism forms a handle part of the catheter.

4. A release mechanism of a delivery system for releasing an object, the object being carried by a catheter on its distal end, the catheter having at least one outer shaft which is retractable toward the proximal end of the catheter for releasing the object, the release mechanism comprising: a stationary cutting device which can cut a proximal section of the outer shaft that is moved toward the proximal end of the catheter into at least two pieces, and a winding device comprising a pair of rollers which winds up the proximal sections of the outer shaft after the proximal sections are cut to retract the outer shaft toward the proximal end of the catheter, at least one of the rollers having an operating element, a spring connecting the operating element with a brake, wherein when the operating element is in a first position, the brake holds an axel of the at least one roller preventing rotation, and wherein when the operating element is in a second position, the brake releases the axel permitting rotation.

5. The release mechanism of claim 4, wherein at least one roller has a smaller diameter on one axial end than on the opposite axial end.

6. The release mechanism of claim 4, wherein the winding device can be hand-driven for winding the outer shaft.

7. The release mechanism of claim 4, wherein the winding device comprises an electric drive for winding the outer shaft.

8. A delivery system for releasing an object carried by a catheter, the delivery system comprising:
a) a catheter having a proximal end, a distal end and at least one retractable outer shaft having a proximal section;
b) a release mechanism for releasing an object carried by the catheter comprising;
a stationary cutting device which can cut a proximal section of the outer shaft that is moved toward the proximal end of the catheter into at least two pieces; and
a winding device comprising a pair of rollers associated with the proximal end of the outer shaft, the winding device being capable of winding up the proximal sections of the outer shaft after the proximal sections are cut so as to retract the outer shaft, at least one of the rollers having an operating element, a spring connecting the operating element with a brake, wherein when the operating element is in a first position, the brake holds an axel of the at least one roller preventing rotation, and wherein when the operating element is in a second position the brake releases the axel permitting rotation.

9. A catheter-based object delivery device for delivering an object, such as a stent, via a catheter, the catheter including a proximal end, a distal end and a hollow outer shaft having a longitudinal axis, the outer shaft being adapted to at least partially contain the object within the distal end, the delivery device comprising a release mechanism associated with the proximal end of the catheter for retracting and retaining the cut portion of the outer shaft, the release mechanism comprising:
a) a stationary cutting device disposed generally in alignment with the longitudinal axis of the outer shaft and adapted for cutting at least a portion of the outer shaft that is moved toward the proximal end of the catheter to form a cut portion made of a first cut part and a second cut part; and,
b) a winding device comprising
a first roller,
(ii) a second roller, and
(iii) a winding mechanism for actuating at least one of the first or second rollers such that the first cut part can be wound at least partially around the first roller and the second cut part can be wound at least partially around the second roller, whereby the outer shaft can be retracted toward the proximal end causing the release of the object from within the outer shaft, at least one of the rollers having an operating element, a spring connecting the operating element with a brake wherein when the operating element is in a first position, the brake holds an axel of the at least one roller preventing rotation, and wherein when the operating element is in a second position, the brake releases the axel permitting rotation.

10. A delivery system for delivering an object, such as a stent, the delivery system comprising:
   a) a catheter having a proximal end, a distal end and a hollow outer shaft having a longitudinal axis, the outer shaft being adapted to at least partially contain the object within the distal end;
   b) a release mechanism associated with the proximal end of the catheter for retracting and retaining a cut portion of the outer shaft so as to release the object, the release mechanism comprising:
      a stationary cutting device disposed generally in alignment with the longitudinal axis of the outer shaft and adapted for cutting at least a portion of the outer shaft that is moved toward the proximal end of the catheter to form a cut portion made of a first cut part and a second cut part; and,
      a winding device comprising
         (i) a first roller,
         (ii) a second roller, and
         (iii) a winding mechanism for actuating at least one of the first or second rollers such that the first cut part can be wound at least partially around the first roller and the second cut part can be wound at least partially around the second roller, whereby the outer shaft can be retracted toward the proximal end and the object released from within the outer shaft, at least one of the rollers having an operating element, a spring connecting the operating element with a brake, wherein when the operating element is in a first position, the brake holds an axel of the at least one roller preventing rotation, and wherein when the operating element is in a second position, the brake releases the axel permitting rotation.

11. The delivery system of claim 10, wherein at least one roller has a smaller diameter on one axial end than on the opposite axial end.

12. The delivery system of claim 10, wherein the winding device can be hand-driven for winding the outer shaft.

13. The delivery system of claim 10, wherein the winding device comprises an electric drive for winding the outer shaft.

14. The delivery system of claim 1 wherein the brake comprises brake shoes and a mating element, and wherein the mating element contacts the brake shoes in the first position and wherein the mating element is not in contact with the brake shoes in the second position.

15. The delivery system of claim 1 further comprising a rotary spring or an electric drive connected to the axel.

16. The delivery system of claim 8 wherein the brake comprises brake shoes and a mating element, and wherein the mating element contacts the brake shoes in the first position and wherein the mating element is not in contact with the brake shoes in the second position.

17. The delivery system of claim 8 further comprising a rotary spring or an electric drive connected to the axel.

18. The delivery system of claim 9 wherein the brake comprises brake shoes and a mating element, and wherein the mating element contacts the brake shoes in the first position and wherein the mating element is not in contact with the brake shoes in the second position.

19. The delivery system of claim 9 further comprising a rotary spring or an electric drive connected to the axel.

20. The delivery system of claim 10 wherein the brake comprises brake shoes and a mating element, and wherein the mating element contacts the brake shoes in the first position and wherein the mating element is not in contact with the brake shoes in the second position.

* * * * *